United States Patent
Koppes et al.

(10) Patent No.: US 6,423,844 B1
(45) Date of Patent: Jul. 23, 2002

(54) PROCESS FOR MAKING 1,2,4-TRIAZOLO[4, 3-A][1,3,5]TRIAZINE-3,5,7-TRIAMINE

(75) Inventors: William M. Koppes; Michael E. Sitzmann, both of Adelphi, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/874,946

(22) Filed: Jun. 6, 2001

(51) Int. Cl.$^7$ .............................................. C07D 487/04
(52) U.S. Cl. ....................................................... 544/198
(58) Field of Search ......................................... 544/198

(56) References Cited

U.S. PATENT DOCUMENTS

| | | | |
|---|---|---|---|
| 3,061,605 A | 10/1962 | D'Alelio | |
| 4,133,674 A | 1/1979 | Cartwright et al. | ............. 71/93 |
| 4,405,619 A | 9/1983 | Heilman et al. | ............. 424/249 |
| 4,605,433 A | 8/1986 | Pearson et al. | ................. 71/93 |
| 4,628,103 A | 12/1986 | Alicot | ......................... 548/266 |
| 4,831,013 A * | 5/1989 | Francis | ........................ 544/251 |
| 4,988,811 A | 1/1991 | Valbusa et al. | ............. 544/207 |
| 5,326,869 A | 7/1994 | Hutton | ........................ 544/209 |
| 5,358,950 A * | 10/1994 | Bru-Magniez et al. | ....... 514/258 |

FOREIGN PATENT DOCUMENTS

WO   WO-95 03806 A1 * 2/1995

OTHER PUBLICATIONS

"Chemistry of Dicyandiamide V. Structures of Guanazo– and Pyro–Guanazoles, and Reaction of Dicyandiamide With 3–Amino–5–Substituted–1,2,4H–Triazoles," Kaiser, et al., May 21, 1953.

"Monotriazolotriazines: A correction to the Product Structure in the Dicyandiamide–Hydrazine Condensation Reaction," Koppes, et al., Aug. 2000.

* cited by examiner

Primary Examiner—Mukund J. Shah
Assistant Examiner—Venkataraman Balasubramanian
(74) Attorney, Agent, or Firm—Mark Homer

(57) ABSTRACT

The present invention is a process for making a 1,2,4-triazolo[4,3-a][1,3,5]triazine-3,5,7-triamine, acid salt and a process for neutralizing the acid salt to make 1,2,4-triazolo[4,3-a][1,3,5]triazine-3,5,7-triamine. 1,2,4-triazolo[4,3-a][1,3,5]triazine-3,5,7-triamine can be used as a precursor for ingredients in propellants, explosives, pyrotechnics, gas generators, pharmaceuticals, and azo dyes. The general process involves ring closure of 2,4-diamino-6-hydrazino-s-triazine with an acid and a chemical of the general formula RCN where the R comprises a leaving group, then neutralizing said acid.

14 Claims, No Drawings

PROCESS FOR MAKING 1,2,4-TRIAZOLO[4, 3-A][1,3,5]TRIAZINE-3,5,7-TRIAMINE

STATEMENT OF GOVERNMENT INTEREST

The invention described herein may be manufactured and used by or for the Government of the United States of America for governmental purposes without payment of any royalties thereon or therefor.

BACKGROUND OF THE INVENTION

1. Field of the Invention

The present invention pertains to the field of synthesis of precursor chemicals for energetic ingredients and more particularly to synthesis of a triazolotriazinetriamine precursor for ingredients in propellants, explosives, pyrotechnics, gas generators, pharmaceuticals, and azo dyes.

2. Brief Description of the Prior Art

Current methods that purport to synthesize 1,2,4-triazolo [4,3-a][1,3,5]triazine-3,5,7-triamine all involve heating dicyandiamide and hydrazine dihydrochloride at elevated temperatures (100 degrees C. or higher) for significant amounts of time in order to condense the dicyandiamide. This method was described by Kaiser et al. in a paper published in the Journal of Organic Chemistry, Vol. 18, 1953, page 1610.

Using this synthesis method theoretically provides for two possible isomeric structures of triazolotriazinetriamine (see I and II below). The first structure is the [4,3-a] triazolotriazinetriamine, pictured below as I. The second structure is the [1,5-a] triazolotriazinetriamine, pictured below as II. The product by Kaiser et al., resulting from the method above, was assigned the structure of I based upon degradation/oxidation studies of the product. However, these types of studies provide for a large degree of uncertainty as to structure.

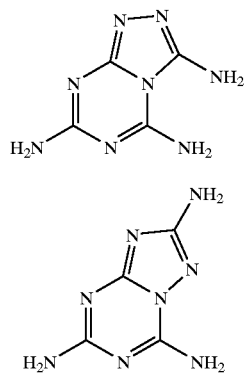

Recently, product derived from the above process was tested using X-ray diffraction, an extremely reliable technique, and, rather than the expected product I as originally reported, it was found that the actual structure of the product was that of II. These findings were presented at the American Chemical Society annual meeting in August of 2000.

The commercial product based upon the above method, sold under the names 3,5,7-triamino-s-triazolo[4,3 -a]-s-triazine or 3,5,7-triamino-1,2,4-triazolo[4,3-a]-1,3,5-triazine, has also been tested via X-ray diffraction and found to be the structure of II. Because of the above error, prior to the present invention, there is, therefore, no known process of synthesizing product I.

The effects of the structural difference between these two products on the chemical and physical properties are of interest in any application of monotriazolotriazine ring systems. Of particular interest for energetic uses of these products would be the energy release in detonation, which correlates to the density of the materials. An analysis of densities and potential energy releases of the products reveals that the product I has a higher potential energy release value than product II that is significant in defense related energetic systems. The product II has also been investigated for use in the dye industry as a chromophore coupled to anthraquinones and indoles, and, therefore, product I should have similar potential uses.

Due to the discovery that the chemical sold as product I is actually product II, and the chemical and physical properties of the two products are significant for many uses, it would be desirable to provide a process for synthesis of product I.

SUMMARY OF THE INVENTION

Accordingly, it is an object of this invention to provide a process to synthesize a 1,2,4-triazolo[4,3-a][1,3,5]triazine-3,5,7-triamine, acid salt.

It is a further object of this invention to provide a process to synthesize 1,2,4-triazolo[4,3-a][1,3,5]triazine-3,5,7-triamine.

This invention accomplishes these objectives and other needs related to synthesis of chemical precursors for energetic ingredients by providing a process to make 1,2,4-triazolo[4,3-a][1,3,5]triazine-3,5,7-triamine comprising the steps of dissolving 2,4-diamino-6-hydrazino-s-triazine with an acid, mixing the dissolved 2,4-diamino-6-hydrazino-s-triazine with a reagent of the formula RCN, wherein R comprises a leaving group, removing acid salt crystals from the solution, and, neutralizing the acid salt crystals by mixing with a substance more basic than 1,2,4-triazolo[4,3-a][1,3,5]triazine-3,5,7-triamine.

DESCRIPTION OF THE PREFERRED EMBODIMENT

The present invention is a process for making a 1,2,4-triazolo[4,3-a][1,3,5]triazine-3,5,7-triamine, acid salt and a process for neutralizing the acid salt to make 1,2,4-triazolo [4,3-a][1,3,5]triazine-3,5,7-triamine. 1,2,4-triazolo[4,3-a][1, 3,5]triazine-3,5,7-triamine can be used as a precursor for ingredients in propellants, explosives, pyrotechnics, gas generators, pharmaceuticals, and azo dyes. The general process involves ring closure of 2,4-diamino-6-hydrazino-s-triazine with an acid and a chemical of the general formula RCN where the R comprises a leaving group, and then neutralizing said acid. Because the hydrazine nitrogen atoms that form the triazole ring are already in place on the 2,4-diamino-6-hydrazino-s-triazine, the final product formed is the desired [4,3-a] isomer, rather than the [1,5-a] isomer produced by the conventional dicyandiamide/ hydrazine dihydrochloride methods. The general formulas for the process are set forth below:

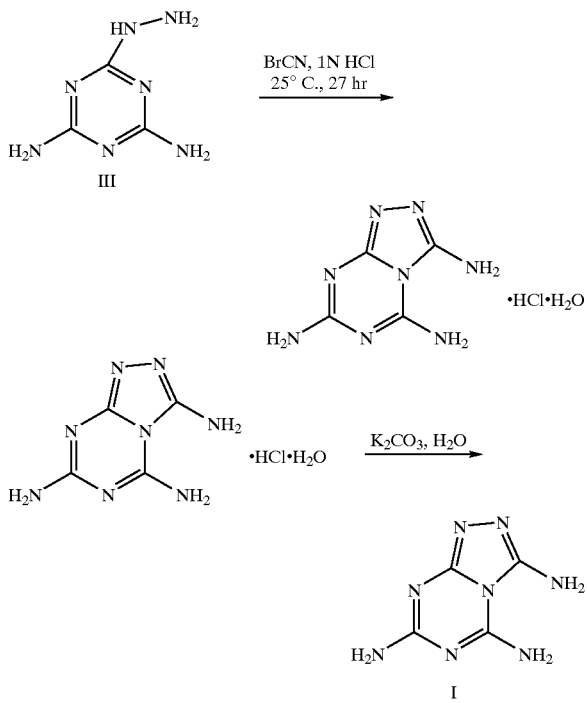

wherein the R comprises a leaving group.

More specifically, first, the invention comprises a process for the preparation of 1,2,4-triazolo[4,3-a][1,3,5]triazine-3,5,7-triamine, acid salt. In order to practice the present invention, one must first obtain or synthesize 2,4-diamino-6-hydrazino-s-triazine. One method for synthesizing this chemical is set forth in U.S. Pat. No. 3,061,605 by D'Alelio. The general method is to effect a reaction between 2,4-diamino-6-chloro-1,3,5-triazine and hydrazine. A specific example is set forth in column 3, lines 60–70 of the above patent and are hereby incorporated by reference. While this particular method of synthesizing 2,4-diamino-6-hydrazino-s-triazine is specifically disclosed, any prior art method of synthesis would be appropriate to practice the present invention.

The first step in the present invention comprises dissolving the 2,4-diamino-6-hydrazino-s-triazine with an acid. This step is preferably carried out at room temperature with an acid that is of sufficient strength to dissolve the 2,4-diamino-6-hydrazino-s-triazine. Many acids can be employed in the present invention, such as sulfuric acid or hydrochloric acid or mixtures of these acids with other solvents such as methanol or ethanol, and may be selected by one skilled in the art. One preferred acid is 1N hydrochloric acid.

The second step comprises mixing the dissolved 2,4-diamino-6-hydrazino-s-triazine with a reagent of the formula RCN, wherein R comprises a leaving group. This reaction will provide the amino triazole ring on the product directly. A leaving group, as used in this application, is a group that can be displaced to give ring closure; that is, produces the amino triazole ring. One preferred leaving group comprises bromine wherein the reagent comprises cyanogen bromide. Although the reaction in this step is acid catalyzed, preferred reaction times range from about twenty hours to about thirty hours in order to allow for the maximum formation of acid salt crystals. It is also preferred that the acid salt crystals be removed after the reaction is substantially complete, approximately thirty hours, to prohibit contamination of the final product with impurities. The crystals may be removed by any normal method, such as filtration, and can then be washed and dried in order to obtain the final acid salt product.

The present invention also comprises a process to take the 1,2,4-triazolo[4,3-a][1,3,5]triazine-3,5,7-triamine, acid salt synthesized above, and neutralize the acid salt crystals in order to obtain a final product of 1,2,4-triazolo[4,3-a][1,3,5]triazine-3,5,7-triamine. This process involves the steps described above as well as the following steps.

First, the acid salt crystals are removed from the solution synthesized above. Then, the acid salt crystals are neutralized by mixing them with a substance more basic than 1,2,4-triazolo[4,3-a][1,3,5]triazine-3,5,7-triamine. This step results in the removal of the acid from the above reaction and provides for a final product of 1,2,4-triazolo[4,3-a][1,3,5]triazine-3,5,7-triamine. The substance used in this final step may be selected by one skilled in the art based upon the basicity of the substance versus the basicity of 1,2,4-triazolo[4,3-a][1,3,5]triazine-3,5,7-triamine. Some examples are potassium carbonate, potassium acetate, sodium bicarbonate, and sodium hydroxide. One preferred substance is potassium carbonate. It is also preferred that the reaction take place in solution, so preferably, water or some other solvent may be added to the salt.

The general nature of the invention having been set forth, the following examples are presented as specific illustrations thereof. It will be understood that the invention is not limited to these specific examples, but can be practiced with various modifications that will be recognized by one of ordinary skill in the art.

EXAMPLE 1

Preparation of 1,2,4-triazolo [4,3-a][1,3,5]triazine-3,5,7-triamine, hydrochloric salt hydrate To 126 g of 1 N hydrochloric acid stirred at 25° C. was added 9.06 g (0.0570 mole) of 2,4-diamino-6-hydrazino-s-triazine [prepared according to G. F. D'alelio, U.S. Pat. No. 3,061,605 (1962)]. The mixture was stirred for 10 minutes, at which time nearly all of the 2,4-diamino-6-hydrazino-s-triazine had dissolved. Cyanogen bromide (9.3 g, 0.0877 mole) was added at one time and, after 5 minutes, all of the material was in solution. After about 1 hour, crystals began to precipitate. After 3 hours, stirring was stopped and the mixture was allowed to stand for an additional 24 hours to continue precipitation of crystals. The crystals were removed by filtration and washed with 2×25 ml cold water. The crystals were air dried and then dried in a vacuum desiccator over Drierite to give 8.60 g (68.4% yield) of product.

IR(KBr): 3300, 3155, 1708, 1695, 1624, 1534, 1490, 1444, 1339, 1173, 1073, 979, 845, 772 cm$^{-1}$.

Anal. Calcd for $C_4H_6N_8$(HCl) ($H_2O$): C, 21.77; H, 4.11; N, 50.79; Cl, 16.07. Found: C, 21.84; H, 4.25; N, 50.02; Cl, 16.02.

EXAMPLE 2

Preparation of 1,2,4-triazolo[4,3-a][1,3,5]triazine-3,5,7-triamine

To 6.86 g (0.031 mole) of 1,2,4-triazolo[4,3-a][1,3,5]triazine-3,5,7-triamine, hydrochloric salt hydrate stirred in 175 ml of water was added 4.40 g (0.031 mole) of potassium carbonate and the mixture was stirred vigorously for 40 minutes. The solid was removed by filtration, washed with water, and dried to give 4.83 g (94%) of 1,2,4-triazolo[4,3-a][1,3,5]triazine-3,5,7-triamine. $^{13}$C NMR(CD$_3$CO$_2$D/D$_2$O, 1:1 by vol): 145.7, 151.1, 151.9, 164.0. $^{13}$C NMR(D$_2$SO$_4$): 133.6, 141.9, 143.1, 149.5. IR(KBr):3413, 3314, 3096, 1654, 1611, 1540, 1480, 1430, 1375, 979, 859, 770 cm$^{-1}$.

Anal. Calcd for C$_4$H$_6$N$_8$: C, 28.92; H, 3.64; N, 67.44. Found: C, 28.64; H, 3.65; N, 66.08.

EXAMPLE 3

Preparation of 1,2,4-triazolo[4,3-a][1,3,5]triazine-3,5,7-triamine, hydrochloric salt hydrate To 0.31 g (0.003 mole) of 37% hydrochloric acid in water (4 ml) and methanol (21 ml) stirred at 25° C. was added 0.42 g (0.003 mole) of 2,4-diamino-6-hydrazino-s-triazine [prepared according to G. F. D'alelio, U.S. Pat. No. 3,061,605 (1962)]. Cyanogen bromide (0.32 g, 0.003 mole) was then added at one time. The solution was held at 77–80° C. for 3 hours, before it was cooled to 25° C. and a small amount of solid was removed by filtration. The volatiles were removed from the filtrate to give 0.60 g of solid that was mainly 1,2,4-triazolo[4,3-a][1,3,5]triazine-3,5,7-triamine, hydrochloric salt hydrate by TLC and IR analyses.

What is described are specific examples of many possible variations on the same invention and are not intended in a limiting sense. The claimed invention can be practiced using other variations not specifically described above.

What is claimed is:

1. A process for the preparation of 1,2,4-triazolo[4,3-a][1,3,5]triazine-3,5,7-triamine, acid salt, comprising the steps of:
    dissolving 2,4-diamino-6-hydrazino-s-triazine with an acid; and,
    mixing the dissolved 2,4-diamino-6-hydrazino-s-triazine with a reagent of the formula RCN, wherein R comprises a leaving group.

2. The process of claim 1, wherein R comprises bromine.

3. The process of claim 2, wherein the acid comprises hydrochloric acid.

4. The process of claim 3, wherein the mixing step further comprises allowing the solution so formed to stand for from about twenty hours to about thirty hours for the precipitation of crystals.

5. The process of claim 3, further comprising the step of removing the crystals from the solution so formed after about thirty hours of standing time.

6. The process of claim 5, wherein the hydrochloric acid comprises a strength of approximately 1N.

7. A process for the preparation of 1,2,4-triazolo[4,3-a][1,3,5]triazine-3,5,7-triamine, comprising the steps of:
    dissolving 2,4-diamino-6-hydrazino-s-triazine with an acid;
    mixing the dissolved 2,4-diamino-6-hydrazino-s-triazine with a reagent of the formula RCN, wherein R comprises a leaving group;
    removing acid salt crystals; and,
    neutralizing the acid salt crystals by mixing with a substance more basic than 1,2,4-triazolo[4,3-a][1,3,5]triazine-3,5,7-triamine.

8. The process of claim 7, wherein R comprises bromine.

9. The process of claim 8, wherein the acid comprises hydrochloric acid.

10. The process of claim 9, wherein the mixing step further comprises allowing the solution so formed to stand for from about twenty hours to about thirty hours for the precipitation of crystals.

11. The process of claim 9, further comprising the step of removing the crystals from the solution so formed after about thirty hours of standing time.

12. The process of claim 11, wherein the substance comprises potassium carbonate and water.

13. The process of claim 12, wherein the hydrochloric acid comprises a strength of approximately 1N.

14. A triazolotriazine product formed by the process of:
    dissolving 2,4-diamino-6-hydrazino-s-triazine with an acid;
    mixing the dissolved 2,4-diamino-6-hydrazino-s-triazine with a reagent of the formula RCN, wherein R comprises a leaving group; and,
    removing acid salt crystals; and,
    neutralizing the acid salt crystals by mixing with a base.

* * * * *